United States Patent
Belliard et al.

(10) Patent No.: US 10,238,433 B2
(45) Date of Patent: Mar. 26, 2019

(54) FIXING DEVICE (75) Inventors: Karl Belliard, La Membrolle sur Longuenee (FR); Gilles Larroque-Lahitette, Baron (FR)

(73) Assignee: Zimmer Spine, Bordeaux (FR)

(*) Notice: Subject to any disclaimer, the term of this patent is extended or adjusted under 35 U.S.C. 154(b) by 1237 days.

(21) Appl. No.: 13/554,196

(22) Filed: Jul. 20, 2012

(65) Prior Publication Data
US 2013/0023878 A1    Jan. 24, 2013

(30) Foreign Application Priority Data

Jul. 21, 2011  (EP) ................................ 11305951
Dec. 13, 2011  (EP) ................................ 11306652

(51) Int. Cl.
*A61B 17/70* (2006.01)
*A61B 17/84* (2006.01)

(52) U.S. Cl.
CPC ........ *A61B 17/7053* (2013.01); *A61B 17/842* (2013.01)

(58) Field of Classification Search
CPC ... A61B 17/7053; A61B 17/82; A61B 17/842; A61B 17/8861
USPC ... 606/60, 263, 265, 270, 277, 71, 300, 301, 606/320, 74, 324, 328
See application file for complete search history.

(56) References Cited

U.S. PATENT DOCUMENTS

| 2,049,361 A | 7/1936 | Johan |
| 4,570,618 A | 2/1986 | Wu |
| 4,887,596 A * | 12/1989 | Sherman ...................... 606/305 |
| 5,030,220 A | 7/1991 | Howland |
| 5,304,178 A | 4/1994 | Stahurski |
| 5,306,275 A * | 4/1994 | Bryan .......................... 606/914 |
| 5,772,663 A | 6/1998 | Whiteside et al. |

(Continued)

FOREIGN PATENT DOCUMENTS

| CN | 103717158 B | 8/2016 |
| EP | 1205152 B1 | 9/2004 |

(Continued)

OTHER PUBLICATIONS

"Chinese Application Serial No. 201280036200.1, Office Action dated Aug. 31, 2015", 8 pgs.

(Continued)

*Primary Examiner* — Matthew J Lawson
*Assistant Examiner* — Amy Sipp
(74) *Attorney, Agent, or Firm* — Schwegman Lundberg & Woessner, P.A.

(57) ABSTRACT

A device for fixing a rod to an osseous structure. The device is configured to receive the rod with the main axis oriented in a first direction. The device includes a main body, a first fastening member directly connected to the main body and accessible from an outer surface of the main body for fastening the rod to the main body, and a second fastening member, also directly connected to the main body, offset with respect to the first fastening member in said first direction, and separately accessible from an outer surface of the main body for fastening to the main body. A flexible elongate member is provided to attach the main body to the osseous structure. The first and second fastening members are arranged so that the flexible elongate member can be fastened adjacent to the rod.

20 Claims, 5 Drawing Sheets

(56) References Cited

U.S. PATENT DOCUMENTS

| | | | |
|---|---|---|---|
| RE36,221 E | 6/1999 | Breard | |
| 5,935,133 A | 8/1999 | Wagner et al. | |
| 5,964,769 A | 10/1999 | Wagner et al. | |
| 6,053,921 A | 4/2000 | Wagner et al. | |
| 6,086,590 A | 7/2000 | Margulies et al. | |
| 6,086,608 A * | 7/2000 | Ek et al. | 606/232 |
| 6,179,838 B1 | 1/2001 | Fiz | |
| 6,277,120 B1 * | 8/2001 | Lawson | 606/263 |
| 6,299,613 B1 | 10/2001 | Ogilvie et al. | |
| 6,309,390 B1 | 10/2001 | Le Couedic et al. | |
| 6,391,030 B1 | 5/2002 | Wagner et al. | |
| 6,514,255 B1 | 2/2003 | Ferree | |
| 6,547,790 B2 | 4/2003 | Harkey, III et al. | |
| 6,605,091 B1 | 8/2003 | Iwanski | |
| 6,641,584 B2 * | 11/2003 | Hashimoto et al. | 606/330 |
| 6,656,185 B2 * | 12/2003 | Gleason et al. | 606/74 |
| 6,682,533 B1 | 1/2004 | Dinsdale et al. | |
| 6,695,852 B2 | 2/2004 | Gleason | |
| 7,144,415 B2 * | 12/2006 | Del Rio et al. | 606/232 |
| 7,481,828 B2 | 1/2009 | Mazda et al. | |
| 7,879,072 B2 * | 2/2011 | Bonutti et al. | 606/232 |
| 7,959,654 B2 | 6/2011 | Mazda et al. | |
| 8,128,635 B2 | 3/2012 | Belliard et al. | |
| 8,172,843 B2 * | 5/2012 | Baccelli et al. | 606/74 |
| 8,313,510 B2 * | 11/2012 | Yuan et al. | 606/246 |
| 8,425,563 B2 * | 4/2013 | Firkins | 606/259 |
| 8,454,657 B2 * | 6/2013 | Raiszadeh | 606/246 |
| 8,636,770 B2 * | 1/2014 | Hestad et al. | 606/248 |
| 8,696,703 B2 * | 4/2014 | Anspach et al. | 606/232 |
| 2002/0040222 A1 * | 4/2002 | Hashimoto et al. | 606/61 |
| 2002/0116013 A1 * | 8/2002 | Gleason et al. | 606/151 |
| 2004/0260285 A1 * | 12/2004 | Steib et al. | 606/61 |
| 2006/0069390 A1 * | 3/2006 | Frigg et al. | 606/61 |
| 2009/0105715 A1 | 4/2009 | Belliard et al. | |
| 2009/0138048 A1 | 5/2009 | Baccelli et al. | |
| 2009/0177233 A1 | 7/2009 | Malek | |
| 2009/0182379 A1 | 7/2009 | Baccelli et al. | |
| 2009/0248077 A1 | 10/2009 | Johns | |
| 2009/0326585 A1 * | 12/2009 | Baccelli et al. | 606/263 |
| 2010/0137913 A1 | 6/2010 | Khatchadourian et al. | |
| 2010/0249845 A1 | 9/2010 | Meunier et al. | |
| 2011/0034956 A1 | 2/2011 | Mazda et al. | |
| 2011/0112581 A1 | 5/2011 | Clement | |
| 2011/0238118 A1 | 9/2011 | Baccelli et al. | |
| 2011/0238125 A1 | 9/2011 | Baccelli et al. | |
| 2011/0301644 A1 | 12/2011 | Belliard | |
| 2012/0022591 A1 | 1/2012 | Baccelli et al. | |
| 2012/0022592 A1 | 1/2012 | Belliard | |
| 2012/0059377 A1 | 3/2012 | Belliard | |
| 2012/0130373 A1 | 5/2012 | Larroque-Lahitette | |
| 2012/0303121 A1 * | 11/2012 | Douget et al. | 623/13.14 |
| 2013/0041410 A1 * | 2/2013 | Hestad et al. | 606/263 |
| 2013/0123841 A1 * | 5/2013 | Lyon | 606/232 |

FOREIGN PATENT DOCUMENTS

| | | |
|---|---|---|
| EP | 2052689 B1 | 12/2011 |
| WO | 0154599 A1 | 8/2001 |
| WO | 0209604 A1 | 2/2002 |
| WO | 0217803 A2 | 4/2002 |
| WO | 2011012690 A1 | 2/2011 |

OTHER PUBLICATIONS

"Chinese Application Serial No. 201280036200.1, Response filed Dec. 30, 2015 to Office Action dated Aug. 31, 2015", 5 pgs.

"European Application Serial No. 12735909.9, Examination Notification Art, 94(3) dated Jun. 1, 2015", 6 pgs.

"European Application Serial No. 12735909.9, Response filed Sep. 14, 2014 to Communication pursuant to Rules 161(1) and 162 EPC dated Feb. 28, 2014", 10 pgs.

"European Application Serial No. 12735909.9, Response filed Oct, 12, 2015 to Examination Notification Art. 94(3) dated Jun. 1, 2015", 5 pgs.

* cited by examiner

FIXING DEVICE

CROSS-REFERENCE TO RELATED APPLICATIONS

This application claims priority to EP11305951.3 filed on Jul. 21, 2011 and EP11306652.6 filed on Dec. 13, 2011, the entire disclosures of which are incorporated herein by reference.

TECHNICAL FIELD

The disclosure relates to a device for fixing a rod to an osseous structure. Such systems and methods may be helpful for holding together a bone and a rod in a desired configuration or in a particular relative position. In particular, said bone may be a transverse process or a lamina of a vertebra.

One field of application for the embodiments in this disclosure is coupling a rod to bones for holding bones in a relative position, for example to aid in the healing of breaks or the positioning of bones in the treatment of spinal deformities or spinal degenerative diseases or trauma diseases, or otherwise to correct abnormal curvatures of the spine. Other bone deficiencies and abnormalities may also benefit from embodiments in this disclosure.

BACKGROUND

One field of application for the invention is fixing bones in a desired position, for example to aid in healing of breaks or in the treatment of scoliosis or otherwise to correct abnormal curvatures of the spine. Other bone deficiencies and abnormalities may also benefit from the invention.

The spine is formed of superposed vertebrae, normally aligned along a vertebral axis, from the lumbar vertebrae to the cervical vertebrae, each having an anterior part, which is the vertebral body, and a posterior part, which is the vertebral arch (or neural arch), the anterior and posterior part enclosing the vertebral foramen. Each vertebral arch is formed by a pair of pedicles and a pair of laminae, and transverse processes and/or a spinous process (or neural spine) project therefrom.

The transverse processes and the spinous process project opposite to the vertebral foramen.

When the vertebrae are articulated with each other, the vertebral bodies form a strong pillar for the support of the head and trunk, and the vertebral foramen constitute a canal for the protection of the spinal cord (or medulla spinalis). In between every pair of vertebrae, there are two apertures, the intervertebral foramina, one on either side, for the transmission of the spinal nerves and vessels.

If the spine of a person has abnormal curvature, the vertebrae are typically inclined relative to one another and relative to said vertebral axis. The lateral edges of the vertebrae on one side are therefore closer together and define a concave outline, while the lateral edges on the other side are farther apart and define a convex outline.

In order to straighten the vertebral column as a remedy for this situation, the lateral edges of the vertebrae on the concave side can be moved away from one another and supported at distances from one another substantially equivalent to the distances between the lateral edges on the convex side. To do so, different kinds of devices may be used.

One such device is the system for fixing a bone to a rod disclosed in international patent application publication WO 2009/047352. It comprises a rod, a blocking body and a conformable elongate member adapted to surround the bone, i.e. to form a loop around it. When using such a system, the elongate member is passed around said bone and through the blocking body and the rod is loaded into the blocking body. The ends of the elongate member are pulled so as to apply tension to the elongate member, and the elongate member and the rod are simultaneously fastened to the blocking body by means of the same fastening system, portion(s) of the elongate member being clamped between the rod and the blocking body. The elongate member and the rod are fastened to the blocking body in one single step.

Another device with the same purpose is described in international patent application publication WO 2011/012690. This device comprises a main body, a flexible elongate member for fixing the main body to an osseous structure, a first fastening member for fastening a portion of the rod to the main body, and a second fastening member for fastening the free end portions of the elongate member to the main body, wherein said second fastening member is distinct from the first fastening member.

In another, similar device known in the art, also comprising a main body, a flexible elongate member for fixing the main body to an osseous structure, a first fastening member for fastening a portion of the rod to the main body, and a second, distinct fastening member for fastening the free end portions of the elongate member to the main body, said second fastening member is laterally offset with respect to the first fastening member, so that a the flexible elongate member is laterally offset with respect to the longitudinal axis of the rod. While such a device facilitates access to the fixation of the elongate member, any force transmitted by the flexible elongate member will induce a significant torsion torque on the rod or the connection of the rod to the fixing device, respectively.

SUMMARY

A first object of the present disclosure is that of providing a device for fixing a rod to an osseous structure, wherein a rod and a flexible member for attaching the device to the osseous structure can be easily fastened to and unfastened from the device separately and substantially independently from each other, in order to facilitate the handling of the device, while preventing that tensions transmitted by the flexible elongate member generate torsion torques around a main axis of the rod.

For this purpose, in at least a first embodiment of the present disclosure, there is provided a device for fixing a rod to an osseous structure, comprising at least a main body, a socket for receiving a rod with a rod longitudinal axis oriented in a first direction, a first fastening member and a second fastening member. The socket is solid with the main body and the first and second fastening members are sized for attachment to the main body. The first fastening member is accessible from an outer surface of the main body and is arranged for fastening a rod received in the socket to the main body. The main body comprises a channel for receiving a flexible member, and the second fastening member which is accessible from an outer surface of the main body is arranged for fastening a flexible member received by said channel, so as to attach the main body to the osseous structure. The first and second fastening members are operable separately from each other, offset with respect to each other in the first direction, and arranged so that the flexible elongate member can be fastened adjacent to the rod. By "adjacent" it is meant, in the present context, that essentially no solid material is interposed between the rod and the flexible member, which, in at least some embodiments, may be directly in contact with each other.

The axial offset and separate access to the first and second fastening members notably allows an operator to release and adjust the tension of the flexible member even while the rod remains fastened to the main body, thus allowing a more precise positioning of the rod with respect to the osseous structure.

However, since the second fastening member is arranged so that said force transmission line of the flexible member can intersect the longitudinal axis of the rod, it is possible to prevent significant torque generation around the rod by traction forces transmitted by the flexible member.

In at least some embodiments, said second fastening member is a compression member configured to fasten the flexible member to the main body by clamping at least one end or both ends of said flexible member against a surface of the main body. When the second fastening member is configured to clamp both ends of said flexible member, it may be configured to clamp both ends to a single surface of the main body, or a first end to a first surface and a second end to an opposite second surface. In particular, the main body may present a lateral orifice through which at least one end of the flexible member may be threaded. In this case, the second fastening member is configured to fasten the flexible member to the main body by clamping said at least one end of said flexible member within said lateral orifice. The flexible member can thus be more unobtrusively fastened. In order to drive the second fastening member against the flexible member when fastening it, and away from said flexible elongate member when unfastening it, while holding a clamping force while the flexible member remains fastened, the second fastening member may have an outer screw thread in engagement with an inner screw thread in the main body. To prevent however that the rotating motion of the second fastening member damages the flexible member by friction, an intermediate part may be interposed between the second fastening member and the flexible member. This intermediate part may be, for example, a ring centered around the screw axis and freely rotatable around the second fastening member.

In at least some embodiments, the first fastening member may be attached to said socket. In particular, said socket may be formed by a recess in the main body, open at least at two opposite ends for receiving part of the rod longitudinally oriented between said two opposite ends for receiving said rod, and said first fastening member may be a pressure member configured to fasten the rod to the main body by clamping the rod against an inner surface of said recess. The rod can thus be introduced into said recess through one of the open ends and reliably fixed within it by the first fastening member. However, in order to also be able to introduce the rod transversally into this recess, said recess may also be laterally open between said two opposite ends. This greatly facilitates operations, in particular when several devices are fastened to the rod. Like the second fastening member, the first fastening member may have an outer screw thread in engagement with an inner screw thread in the main body, in order to drive the first fastening member against the rod when fastening it, and away from said rod when unfastening it, while holding a clamping force while the rod remains fastened.

Alternatively, however, in at least some other embodiments, the first fastening member may constitute at least part of said socket. In particular, said first fastening member may be a clamp with two hinged parts and a closing element configured to close the two hinged parts against each other, this clamp being configured to receive the rod between the two hinged parts. The closing element, which can be a screw, may be located between proximal ends of the hinged parts, to close the clamp by pushing on the proximal ends, or, alternatively, it may be located between distal ends of the hinged parts, to close the clamp by pulling at the distal ends. To simplify the device, one of said two hinged parts may be solid with the main body.

The present disclosure also relates to an assembly comprising such a fixing device, a rod fastened to the main body, by the first fastening member, with the rod longitudinal axis oriented in a first direction, and a flexible elongate member fastened to the main body, adjacently to the rod, by the second fastening member, for attaching the main body to the osseous structure.

The above summary of exemplary embodiments is not intended to describe each disclosed embodiment or every implementation of the invention. The technical features cited above as well as those of the exemplary embodiments described below may be combined with each other and then constitute further embodiments of the disclosed and claimed subject matter. In particular, selected features of any illustrative embodiment within this specification may be incorporated into an additional embodiment unless clearly stated to the contrary.

BRIEF DESCRIPTION OF THE DRAWINGS

The invention may be more completely understood in consideration of the following detailed description of various embodiments in connection with the accompanying drawings, in which.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the invention.

DETAILED DESCRIPTION

For the following defined terms, these definitions shall be applied, unless a different definition is given in the claims or elsewhere in this specification.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 1:
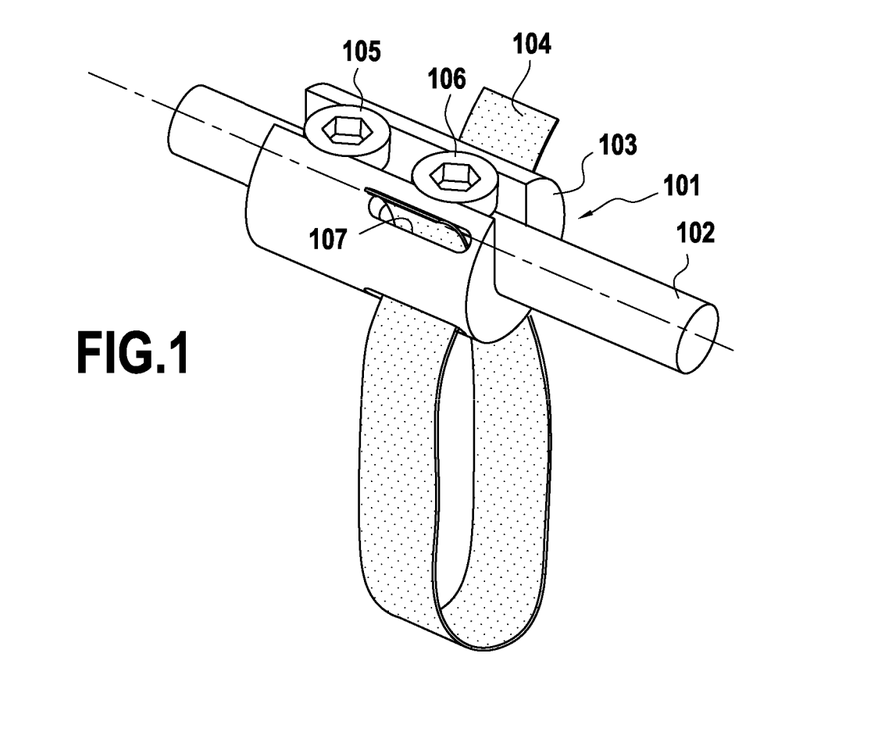
FIG. 1 is a perspective view of a fixing device according to a first embodiment.

In the first embodiment illustrated in FIG. 1, a fixing device 101 is fastened to a rod 102 and an elongated flexible member 104 to form the illustrated assembly. This fixing device 101 comprises a main body 103. The main body 103 presents a recess, which is open at two opposite ends, forming a socket for receiving part of the rod 102 longitudinally between the two opposite ends. The recess is also open laterally between the two opposite ends, so that the rod 102 can be introduced laterally into said recess and not only axially through either one of the two opposite ends. The flexible elongate member 104, in the form of a flexible ligature band, is suitable for fastening the fixing device 101, with the rod 102, to an osseous structure (not illustrated), such as, for example, a vertebra, by tightening an intermediate segment of this flexible elongate member around at least part of said osseous structure.

This fixing device 101 also comprises a first fastening member 105 and a second fastening member 106, directly connected to the main body 103. The first and second fastening members 105, 106 being distinct and separately accessible from the outside of the main body 103, they can be tightened and untightened independently from each other, allowing independent fastening and unfastening of the rod 102 and the flexible elongate member 104.

In the first embodiment illustrated in FIG. 1, the first fastening member 105 and the second fastening member 106 are offset with respect to each other in the direction of the longitudinal axis X of the rod 102. However, both fastening members 105, 106 are arranged along said longitudinal axis X, so that the flexible elongate member 104 can be fastened so as to run adjacent to the rod 102. The first fastening member 105, which in this first embodiment is shaped as a lock screw with an outer screw thread in engagement with an inner screw thread in the lateral opening of the main body 103, also fastens the main body 103 to the rod 102 by clamping the rod 102 against a surface of the recess. The second fastening member 106, which is also shaped as a lock screw, with an outer screw thread in engagement with an inner screw thread in the lateral opening of the main body 103 fastens both ends of the flexible elongate member 104 by clamping them against opposite internal surfaces in the main body 103. The main body 103 presents a first orifice 107 at one side of the second fastening member 106, and a second orifice (not shown) at the opposite side of the second fastening member 106, forming channels for receiving the flexible member 104. A first end of the flexible elongate member 104 is threaded through said first orifice 107, and a second end of the flexible elongate member 104 is threaded through the second orifice (not shown). Because in this first embodiment the flexible elongate member 104 is not significantly offset laterally with respect to the rod 102, torsional torques in the fixing device 101 are minimized. Within the main body 103, both ends of the flexible elongate member 104 can be threaded to the same side of the rod 102 within the recess, or, if necessary, each end may be threaded to one respective side of the rod 102, thus straddling the rod 102 within the recess and further minimizing torsional torques.

Figure 2:
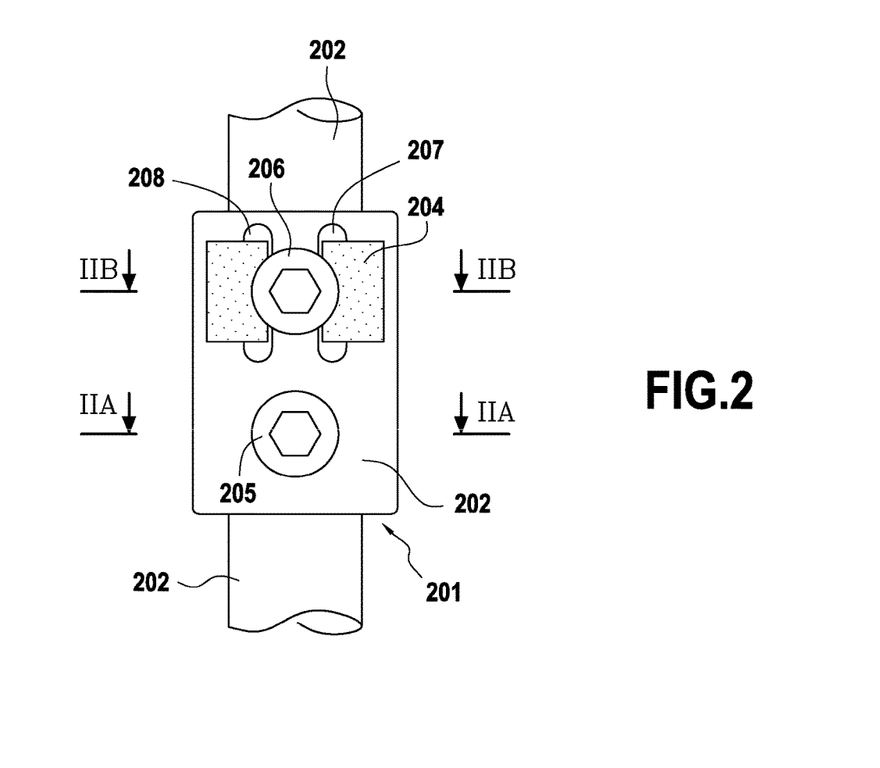
FIG. 2 is a top view of a fixing device according to a second embodiment.
Figure 2A:
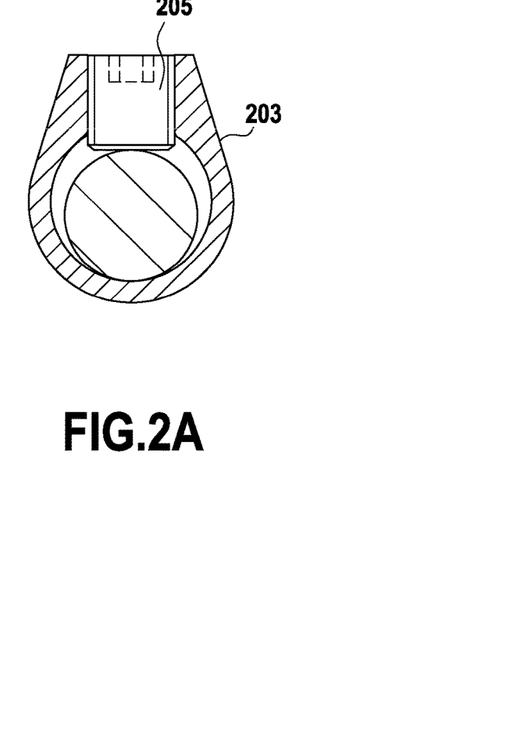
FIGS. 2A and 2B are transversal cut views of the fixing device of the second embodiment through planes IIA-IIA and IIB-IIB of FIG. 3.
Figure 2B:
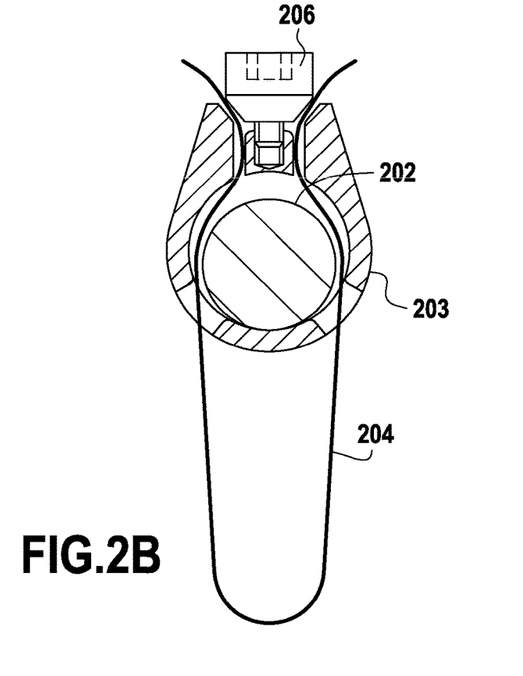

In a fixing device 201 according to a second embodiment, illustrated in FIGS. 2, 2A and 2B, the first fastening member 205 and the second fastening member 206 are also aligned and offset with respect to each other in parallel to the longitudinal axis 202 of the rod 202. However, in this second embodiment, the recess in the main body 203 is not completely open laterally between the two opposite ends, so that the rod 202 can only be introduced axially into the main body 203. The first and second fastening members 205, 206 are also shaped as lock screws in this second embodiment. In this second embodiment, their outer screw threads are in engagement with inner screw threads in respective lateral orifices of the main body 203. As in the previous embodiment, the first fastening member 205 fastens the main body 203 to the rod 202 by clamping the rod 202 against a surface of the recess, and the second fastening member 206 fastens both ends of the flexible member 204 by clamping them against opposite internal surfaces in the main body 203.

As in the first embodiment, a first end of the elongated flexible member 204 is threaded through a first orifice 207 at one side of the second fastening member 206 and a second end is threaded through a second orifice 208 at the opposite side of the second fastening member 206. Within the main body 203, both ends of the flexible elongate member 204 can be threaded to the same side of the rod 202 within the recess, or, if necessary, each end may be threaded to one respective side of the rod 202, thus straddling the rod 202 within the recess and further minimizing torsional torques.

Figure 3:
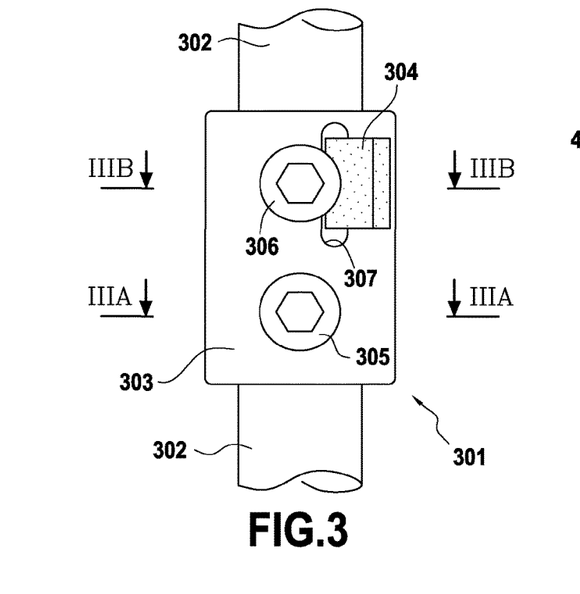
FIG. 3 is a top view of a fixing device according to a third embodiment.
Figure 3A:
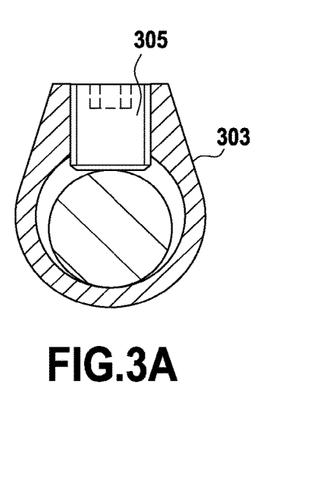
FIGS. 3A and 3B are transversal cut views of the fixing device according to the third embodiment through planes IIIA-IIIA and IIIB-IIIB of FIG. 3.
Figure 3B:
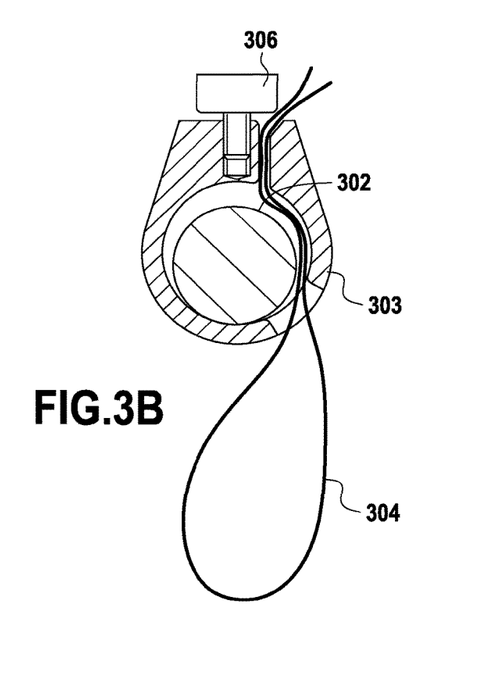

However, as seen in the third embodiment illustrated in FIGS. 3, 3A and 3B, in another fixing device 301, the main body 303 may have a simplified shape with a channel for receiving the flexible member 304 comprising a single orifice 307 for both ends of the flexible member 304 at one side of the second fastening member 306. As in the first and second embodiments, however, within the recess it is still possible to choose between threading both ends of the flexible elongate member 304 to the same side of the rod 302, or threading each end to one respective side of the rod 302. The other elements of this third embodiment, such as the first fastening member 305, shown in particular in FIG. 3A, may be identical to those of the second embodiment.

Figure 4:
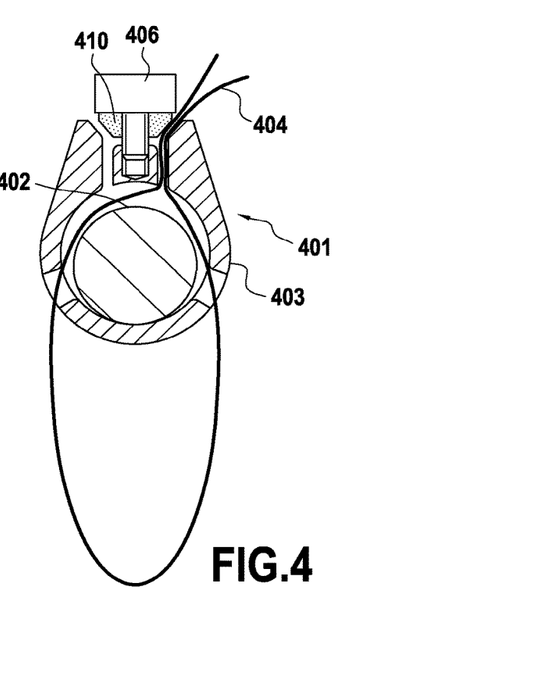
FIG. 4 is a transversal cut view of a fixing device according to a fourth embodiment.

An inconvenience of using a locking screw for fastening the flexible elongate member is that the rotation of the locking screw during fastening and unfastening may cause significant friction between the lockscrew and the flexible elongate member, possibly damaging the latter. To prevent, or at least minimize this friction, in a fourth embodiment, illustrated in FIG. 4, an intermediate part 409, shaped as a ring centered around the screw axis of the second fastening member 406 and freely rotatable around it, is interposed between said second fastening member 406 and the two ends of the flexible elongate member 404. This fourth embodiment can otherwise be analogous to the second embodiment.

Figure 5:
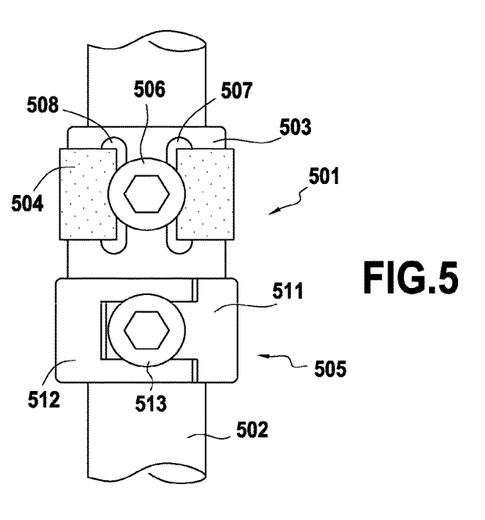
FIGS. 5, 6 and 7 are, respectively, top, side and front views of a fixing device according to a fifth embodiment.
Figure 6:
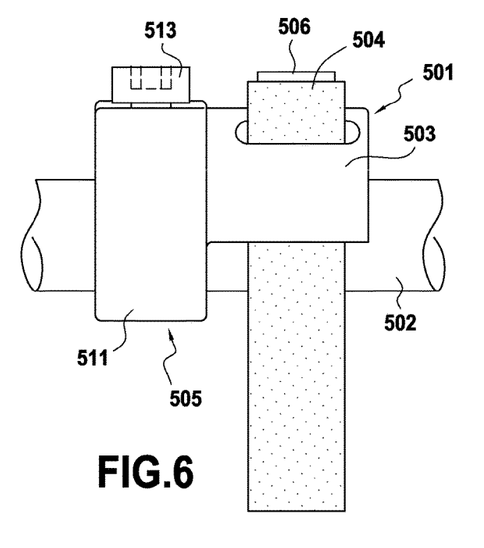
Figure 7:
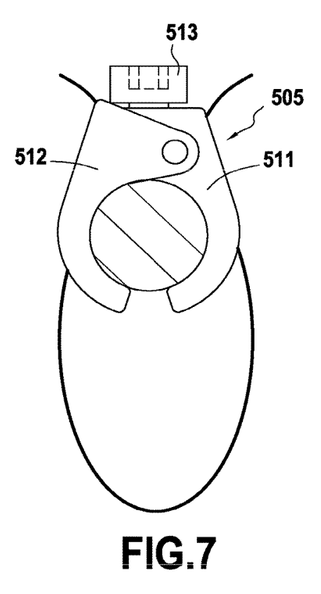

While in these first four embodiments the first fastening member is a lockscrew, alternative means can also be used, as shown for example in the fifth embodiment, illustrated in FIGS. 5 to 7. In the rod fixing device 501 of this fifth embodiment, the socket for receiving the rod 502 is formed by a first fastening member 505, shaped as a clamp, which comprises a first part 511 solid with the main body 503, and a second part 512 hinged to the first part 511. The rod 502 can be received between the first and second parts 511,512 which can then be closed against each other and around the rod 502 by tightening a screw 513 located behind the hinge, between the proximal ends of the first and second parts 511, 512, to fasten the main body 503 to the rod 502. As in the second embodiment, the rod fixing device 501 also comprises a second fastening member 506, shaped as a lockscrew, to fasten both ends of the flexible member 504 by clamping them against opposite internal surfaces in the main body 503, within respective orifices 507, 508 forming channels through which those ends are threaded.

Figure 8:
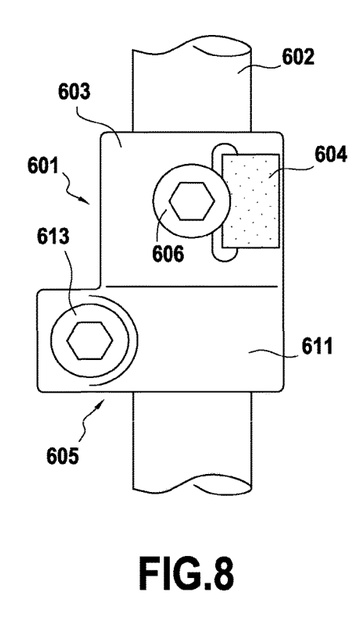
FIGS. 8 and 9 are, respectively, top and side views of a fixing device according to a sixth embodiment.
Figure 9:
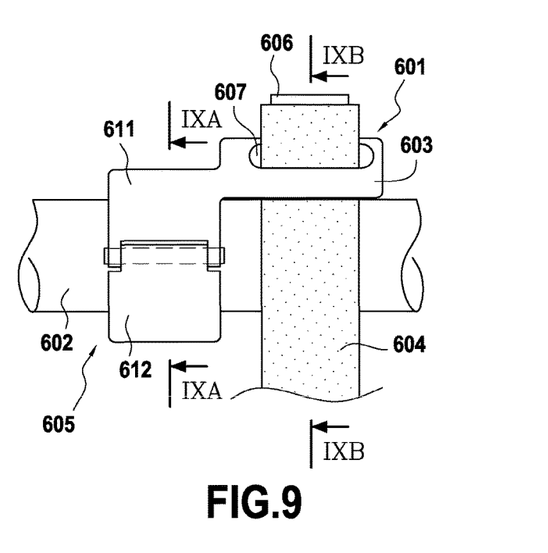
Figure 9A:
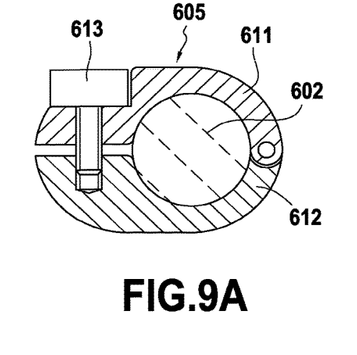
FIGS. 9A and 9B are transversal cut views of the fixing device of the sixth embodiment through planes IXA-IXA and IXB-IXB of FIG. 9.
Figure 9B:
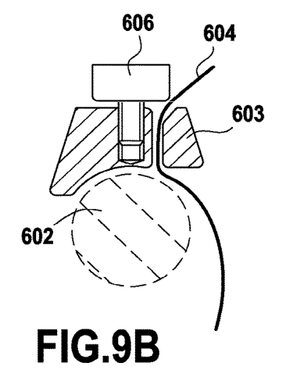

A sixth embodiment with an alternative clamp shape for the first fastening member is illustrated in FIGS. 8, 9A and 9B. In this rod fixing device 601, a first fastening member 605 is also shaped as a clamp comprising a first part 611 solid with the main body 603, and a second part 612 hinged to the first part 611. As in the fifth embodiment, the rod 602 can be received between the first and second parts 611,612 which can then be closed against each other and around the rod 602 by tightening a screw 613. However, in this sixth embodiment, the screw 613 is located opposite to the hinge, linking the distal ends of the first and second parts 611, 612. As in the third embodiment, the rod fixing device 601 also comprises a second fastening member 606, shaped as a lockscrew, to fasten both ends of the flexible elongate member 604 by clamping them against an internal surface in the main body 603, within a channel comprising a single orifice 607 through which both ends are threaded.

Those skilled in the art will recognize that the present invention may be manifested in a variety of forms other than the specific embodiments described and contemplated herein. Accordingly, departure in form and detail may be made without departing from the scope of the present invention as described in the appended claims.

What is claimed:

1. A fixing device for fixing a rod to an osseous structure, the device comprising:
    a main body;
    a socket for receiving a rod with a rod longitudinal axis oriented in a first direction, the socket being solid with the main body;
    a first fastening member; and
    a second fastening member;
    wherein the first and second fastening members are sized for attachment to the main body;
    wherein the first fastening member is accessible from an outer surface of the main body and is arranged for fastening a rod received in the socket to the main body;
    wherein the main body comprises a channel for receiving a flexible member;
    the second fastening member being accessible from an outer surface of the main body and being arranged for fastening the flexible member received by the channel;
    wherein the first and second fastening members are operable independently from each other;
    wherein the first and second fastening members are offset with respect to each other in the first direction; and
    wherein the second fastening member, the channel for receiving a flexible member and the socket are arranged such that the flexible elongate member can be fastened adjacent to the rod.

2. The fixing device of claim 1, wherein said second fastening member is a compression member configured to fasten the flexible member to the main body by clamping at least one end of said flexible member against a surface of the main body with the rod.

3. The fixing device of claim 2, wherein said second fastening member is a compression member configured to fasten the flexible member to the main body by clamping two opposite ends of said flexible member against a surface of the main body with the rod.

4. The fixing device of claim 3, wherein the second fastening member is configured to fasten a first end of said flexible member against a first surface of the main body, and a second end of said flexible member against a second surface of the main body, opposite to the first surface, with the rod.

5. The fixing device of claim 3, wherein the second fastening member is configured to fasten both opposite ends of said flexible member together again a single surface of the main body.

6. The fixing device of claim 2, wherein at least one end of the flexible member is threaded through a lateral orifice in the main body.

7. The fixing device of claim 6, wherein the second fastening member is configured to fasten the flexible member to the main body by clamping said at least one end of said flexible member within said lateral orifice.

8. The fixing device of claim 7, wherein said second fastening member has an outer screw thread in engagement with an inner screw thread in the main body.

9. The fixing device of claim 8, further comprising an intermediate part between the second fastening member and the flexible member.

10. The fixing device of claim 1, wherein the first fastening member is attached to said socket.

11. The fixing device of claim 10, wherein said socket is formed by a recess in said main body, said recess being open at least at two opposite ends for receiving part of the rod longitudinally oriented between said two opposite ends for receiving said rod, and said first fastening member is a pressure member configured to lock the rod to the main body by clamping the rod against an inner surface of said recess.

12. The fixing device of claim 11, wherein said recess is also open laterally between said two opposite ends.

13. The fixing device of claim 12, wherein said first fastening member has an outer screw thread in engagement with an inner screw thread in the main body.

14. An assembly comprising:
    a fixing device according to claim 1;
    a rod fastened to the main body by the first fastening member with the rod longitudinal axis oriented in a first direction; and
    a flexible member fastened to the main body adjacent to the rod by the second fastening member for attaching the main body to the osseous structure.

15. The fixing device of claim 1, wherein the first fastening member constitutes at least a part of said socket.

16. The fixing device of claim 15, wherein said first fastening member is a clamp with two hinged parts and a closing element configured to close the two hinged parts against each other, this clamp being configured to receive the rod between the two hinged parts.

17. The fixing device of claim 16, wherein said closing element is located between proximal ends of the hinged parts.

18. The fixing device of claim 16, wherein said closing element is located between distal ends of the hinged parts.

19. The fixing device of claim 16, wherein one of said two hinged parts is solid with the main body.

20. The fixing device of claim 16, wherein said closing element is a screw.

\* \* \* \* \*

UNITED STATES PATENT AND TRADEMARK OFFICE
CERTIFICATE OF CORRECTION

PATENT NO. : 10,238,433 B2
APPLICATION NO. : 13/554196
DATED : March 26, 2019
INVENTOR(S) : Belliard et al.

It is certified that error appears in the above-identified patent and that said Letters Patent is hereby corrected as shown below:

On the Title Page

On page 2, in Column 2, item (56), under "Other Publications", Line 6, delete "14, 2014" and insert --10, 2014-- therefor In the Claims In Column 7, Line 61, in Claim 1, after "flexible", delete "elongate"

In Column 8, Line 14, in Claim 5, delete "again" and insert --against-- therefor Signed and Sealed this
Twenty-first Day of April, 2020

Andrei Iancu
*Director of the United States Patent and Trademark Office*